Figure 1:
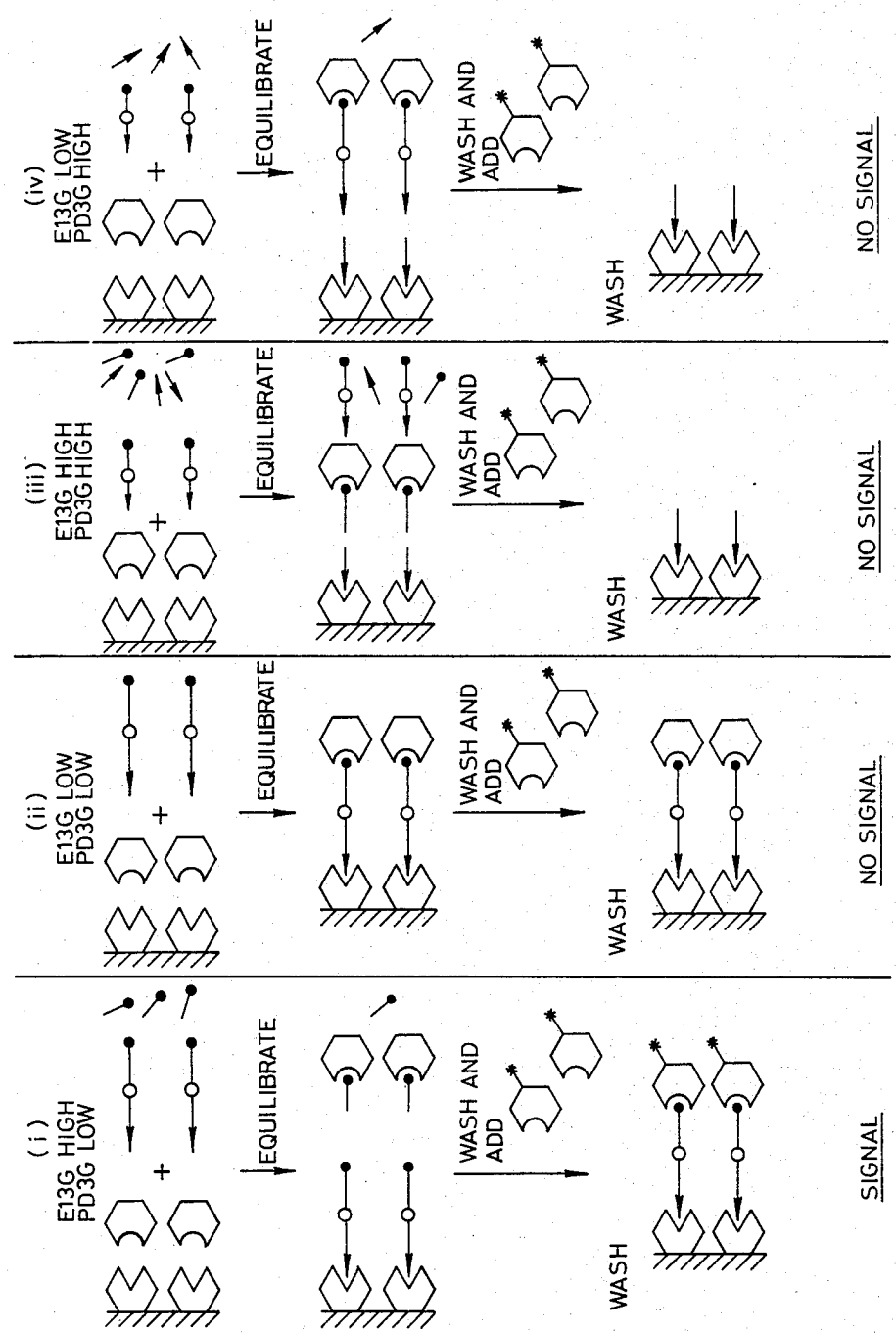

United States Patent [19]

Baker et al.

[11] Patent Number: 4,508,830
[45] Date of Patent: Apr. 2, 1985

[54] ASSAY

[76] Inventors: Terence S. Baker, 70 Welley Rd., Wraysbrugy, Staines, Middlesex, TW19 5EP, England; William F. Couslon, 1 Grayson's Close, Rayleigh, Essex, England

[21] Appl. No.: 464,143

[22] Filed: Feb. 7, 1983

[30] Foreign Application Priority Data

Feb. 10, 1982 [GB] United Kingdom ............... 8203906

[51] Int. Cl.$^3$ ............................................. G01N 33/54
[52] U.S. Cl. .................................... 436/510; 436/518; 436/532; 436/808; 436/809; 436/814; 436/817; 436/543; 435/7
[58] Field of Search ............... 436/510, 532, 518, 808, 436/809, 814, 817; 435/7

[56] References Cited

U.S. PATENT DOCUMENTS 4,048,298 9/1977 Neswender .......................... 424/1.5

FOREIGN PATENT DOCUMENTS

| 2034466 | 6/1980 | United Kingdom . |
| 2029011 | 12/1980 | United Kingdom .................... 435/7 |
| 2051357 | 1/1981 | United Kingdom ................ 436/531 |
| 2078953 | 1/1982 | United Kingdom . |

OTHER PUBLICATIONS

Weerasekera et al., J. Steroid. Biochem. 18(4), (1983) 465-470.
"Structural Concepts in Immunology and Immunochemistry", Kabat, E. A., Second Edition, Published by Holt, Rienhard and Winston, p. 8, Line 21-29.
"Essential Immunology", Roitt, I., Third Edition, Published by Blackwell, pp. 15-16.

Primary Examiner—Christine M. Nucker
Attorney, Agent, or Firm—Cushman, Darby & Cushman

[57] ABSTRACT

There is described an assay for determining the relative concentrations of two antigenic solutes in a sample. The assay involves a first antibody to the first antigenic solute, a second antibody to the second antigenic solute and a ligand molecule having substituents to which the first and second antibodies may bind. The second antibody is immobilized upon a solid phase support and the other components are in solution. The components are mixed with a sample containing the antigenic solutes causing competition between the ligand molecule and each of the antigenic solutes for binding to the first and second antibodies. In the situation where there is a relatively higher concentration of the first antigenic solute to the second antigenic solute in the sample, a significant number of the ligand molecules become attached to the solid phase via the second antibody yet are capable of binding to a labelled antibody having the same specificity as the first antibody. The presence of labelled antibody bound to the solid phase support is indicative of the above mentioned situation. A method is described using the assay for determining the fertile period of the menstrual cycle by monitoring the relative concentration of oestrone-3-glucuronide and preganediol-3-glucuronide in urine. A reagent kit for use in performing the assay and method is described. A ligand molecule is described which comprises two, different antigenic radicals bound together through a bridging support molecule in which the bridging support molecule is a divalent radical derived from an organic compound having two reactive functional groups.

14 Claims, 6 Drawing Figures

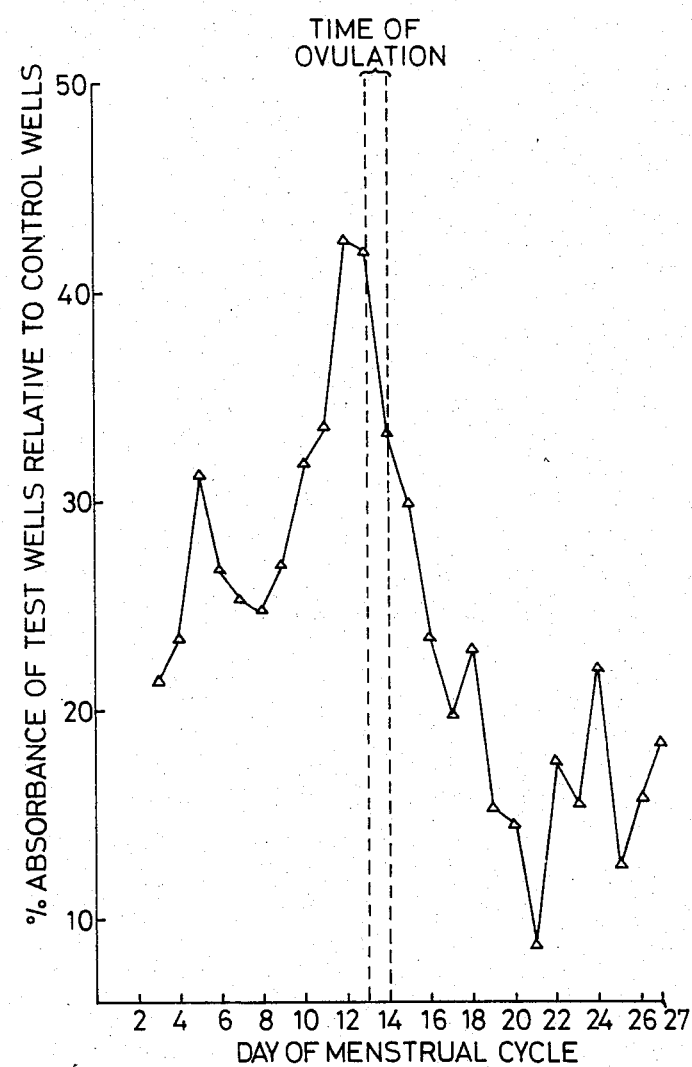

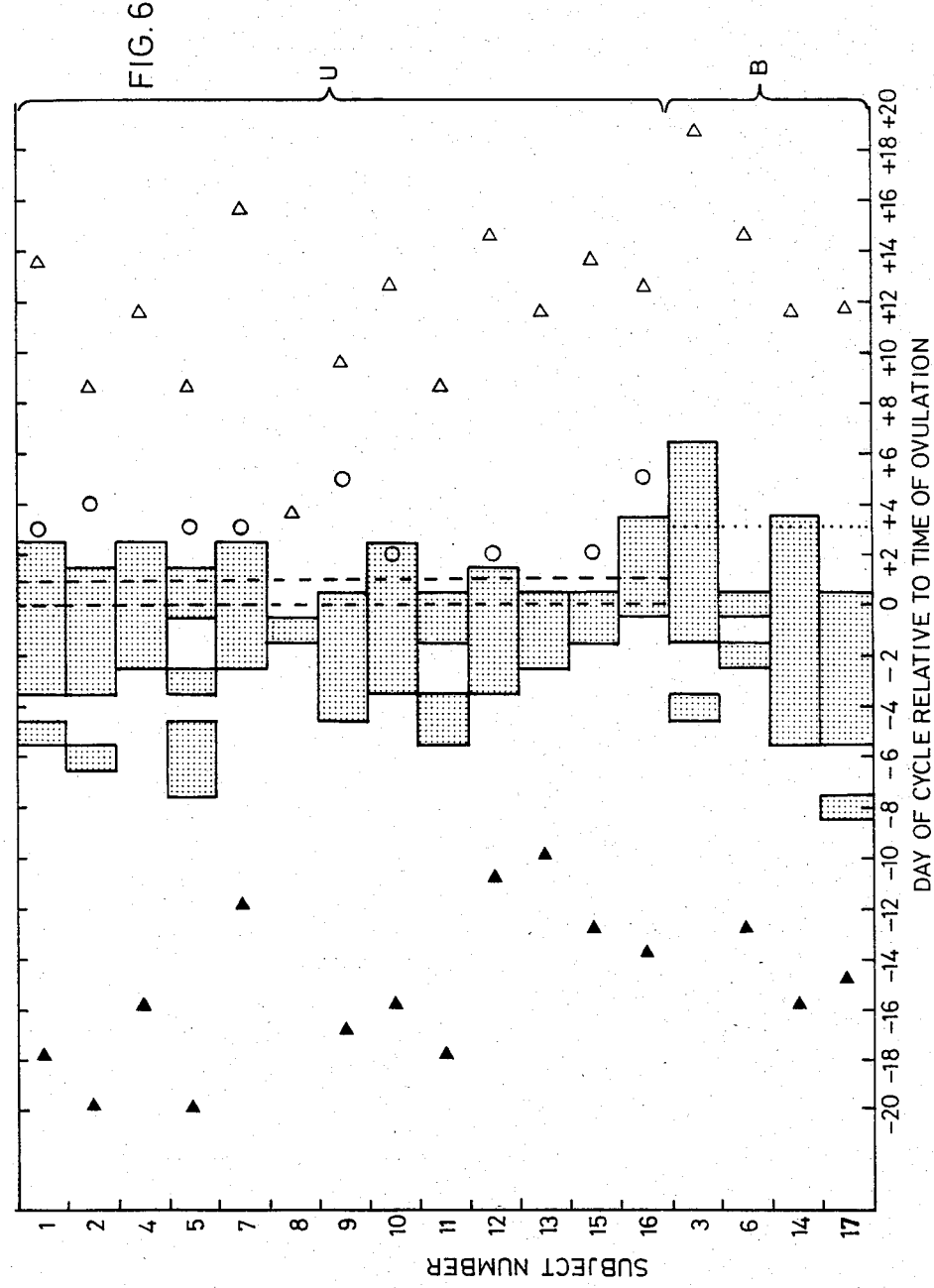

ASSAY

This invention relates to an immunoassay. In particular it concerns an assay for determining the relative concentrations of two antigenic solutes. A particular example is given of the use of the assay for detecting in a sample the relative concentrations of 3-hydroxy-oestra-1,3,5(10)-triene-17-one-3-$\beta$-D-glucupyranosiduronic acid (hereafter referred to as oestrone-3-glucuronide or E13G) and 5$\beta$-pregnane-3$\alpha$,20$\alpha$-diol 3$\alpha$-$\beta$-D-glucupyranosiduronic acid (hereafter referred to as preganediol-3-glucuronide or PD3G).

There has long been a need for a simple but reliable technique to indicate the fertile period of the menstrual cycle (i.e. the period in which viable sperm and a viable ovum may be present together in the reproductive tract of the female). Many women, for clinical or religious reasons, are unable to avail themselves of the wide variety of contraceptive devices and compositions presently available. A technique whereby the fertile period of the menstrual cycle could be ascertained would enable a woman to avoid conception by abstinence from intercourse during her fertile period. The same technique for indicating the fertile period would also assist in cases where conception is sought.

The menstrual cycle is governed by the rhythmic release of hormones both from the adenohypophysis (the anterior lobe of the pituitary gland) and from the ovaries. During each menstrual cycle, as a result of a complex interaction between these hormones and specific cells in the ovaries, the adenohypophysis and certain areas of the brain, an ovum is released from the ovaries and the lining of the uterus (endometrium) is prepared in readiness for pregnancy. The ovaries comprise fibrous tissue stroma containing a number of ovarian follicles in which ova form. The release of follicle stimulating hormone (FSH) from the adenohypophysis causes the cells of the ovarian stroma surrounding a follicle in the ovary to proliferate and form a cavity. During the development of the follicle a group of steroid hormones, the oestrogens, are produced.

Ovulation occurs when rupture of the follicle is stimulated by the release of luteinizing hormone (LH) from the adenohypophysis. Once the ovum has been discharged into the abdominal cavity to begin its passage down the fallopian tube, the remaining cells of the follicle form the corpus luteum. The corpus luteum elaborates a second group of steroid hormones, the progestins.

The menstrual cycle may be notionally divided into a follicular phase (up to ovulation) and a luteal phase (after ovulation). In the follicular phase the ripening ovarian follicle excretes oestrogens which cause the endometrium to regenerate following its loss during the previous period. Upon ovulation the excretion of progestins by the corpus luteum instigates the formation of endometrial mucosa and thereby prepares the uterus for the implantation of an ovum if fertilisation has occurred during the passage of the ovum down the fallopian tube. If fertilisation has not occurred and an ovum does not implant in the uterus the corpus luteum degenerates and the level of progestins decreases leading to degeneration of the endometrium and to bleeding. The full cycle takes approximately 28 days to complete.

The ovary elaborates three oestrogen compounds; oestradiol, oestriol and oestrone. Oestradiol is the most potent oestrogen and is readily oxidised to oestrone by the body. Oestrone is hydroxylated to form oestriol. All three of these steroids are present in the urine of women as glucuronide derivatives.

The naturally occuring progestin is progesterone. The level of progestrone in the blood reaches a peak two or more days after ovulation. It is rapidly metabolised to pregnanediol which is excreted in the urine as a glucuronide derivative.

The levels of oestrogen and progestin metabolites in the urine may be used to monitor the progress of the menstrual cycle. In particular the ratio of oestrone-3-glucuronide to pregnanediol-3-glucuronide, which is low in the first week of the cycle, starts to increase several days (for example 2 to 5 days) before ovulation and reaches a peak value around the time of ovulation (the peri-ovulatory phase). The ratio then decreases rapidly to reach low values by two days after the time of ovulation. Since that part of the menstrual cycle, when the ratio is elevated, corresponds to the fertile period of the cycle, an assay for indicating raised values of the ratio is clearly invaluable.

If the assay is cheap and simple it may form the basis of an extremely useful test for fertility.

In our British patent specification No. GB 2029011B, we describe a reagent system and a method for determining this ratio. The specification describes an immunochemical method for detecting the fertile period of the menstrual cycle, by determining the relative concentrations, in urine, of the two hormonal metabolites, oestrone-3-glucuronide and pregnanediol-3-glucuronide. The method depends upon determining the extent to which an immunocomplex dissociates in the presence of the two metabolites.

The immunocomplex described in our earlier specification comprises; a solid phase having irreversibly attached to it antibodies to pregnanediol-3-glucuronide; a bifunctional ligand comprising oestrone-3-glucuronide and pregnanediol-3-glucuronide moieties irreversibly bound to bovine serum albumin; and antibodies to oestrone-3-glucuronide. The ligand is bound reversibly by an immunochemical bond to the pregnanediol-3-glucuronide antibody attached to the solid support, and the oestrone-3-glucuronide antibody is bound reversibly by an immunochemical bond to the ligand.

In the method the immunocomplex is incubated with urine. The metabolites in the urine compete for the antibodies causing the immunocomplex to dissociate partially. The solid phase is then washed. The number of exposed oestrone-3-glucuronide moieties remaining bound to the solid phase depends upon the ratio of oestrone-3-glucuronide to pregnanediol-3-glucuronide in the urine. The number of exposed oestrone-3-glucuronide moieties may be determined with an enzyme labelled antibody to oestrone-3-glucuronide.

The reagent system and method described in British patent specification No. 2029011B, though effective, have some limitations.

The oestrone-3-glucuronide and pregnanediol-3-glucuronide moieties are bound to a support protein (in the specific embodiment, bovine serum albumin) to form a notionally bifunctional ligand. It is an essential requirement that the bonds formed between the ligand and the anti-pregnanediol-3-glucuronide bound to the solid phase and the bonds formed between the ligand and the anti-oestrone-3-glucuronide are reversible. It has now been found that these bonds are only partially reversible with the result that the immunocomplex does not exhibit adequate dissociation when incubated with a solution containing oestrone-3-glucuronide and pregnanediol-3-glucuronide. This may be due to a multivalent reaction of the ligand caused by the attachment of more than one of each moiety to the support protein.

There may also be an immunological reaction between the non-steroidal determinants on the bovine serum albumin itself and antibodies attached to the solid phase.

In addition a problem arises from the disparate concentrations of oestrone-3-glucuronide and pregnanediol-3-glucuronide present in female urine. Typically the concentration of pregnanediol-3-glucuronide is 10–50 times greater than that of oestrone-3-glucuronide. The reagent system and method described in specification No. 2029011B exhibit similar sensitivity to both oestrone-3-glucuronide and pregnanediol-3-glucuronide. This may lead to deceptive test results.

The method disclosed in GB No. 2029011B is referred to hereafter as a dual analyte assay since the method is one which involves the simultaneous assay of two analytes. In particular the dual analyte assay determines the concentration of one analyte relative to a second analyte. The determination of the relative concentrations is however a complex function of the ratio of the concentration of the two analytes and the dual analyte assay is therefore preferably used to indicate when a threshold value in the ratio has been reached or exceeded.

The object of the present invention is to provide a dual analyte assay which allows for the establishment of an adequate competitive equilibrium and which affords an increased sensitivity to an antigenic solute which is present in a markedly lower concentration than a second antigenic solute.

According to the present invention we provide an assay involving the following components;

a sample solution containing a first and a second antigenic solute;

a first antibody capable of reversibly binding to a determinant of the first antigenic solute, the first antibody being in solution;

a second antibody capable of reversibly binding to a determinant of the second antigenic solute, the second antibody being irreversibly bound to a solid phase support;

a ligand molecule comprising a first antigen to which the first antibody is capable of reversibly binding and a second antigen to which the second antibody is capable of reversibly binding, the first and second antigens being irreversibly bound together through a bridging support molecule, the ligand molecule being in solution; and a labelled antibody capable of reversibly binding to the first antigen, the assay comprising the steps of;

forming a mixture of the sample solution, the first antibody, the second antibody and the ligand molecule, provided that the first antibody, the second antibody and the ligand molecule are not all mixed with each other prior to admixture of the sample solution;

incubating the said mixture, thereby allowing competition between the ligand molecule and the first antigenic solute for association with the first antibody, and allowing competition between the ligand molecule and the second antigenic solute for association with the second antibody, placing the solid phase support in contact with the labelled antibody, thereby allowing association between the labelled antibody and any unbound first antigen; and determining the amount of labelled antibody bound to the solid phase support through the ligand molecule and the second antibody.

Preferably, the ligand molecule comprises one first antigen and one second antigen and two antigens being irreversibly bound together through a bridging support molecule. The presence of only one first antigen and one second antigen in the ligand molecule ensures an effective competitive reaction.

In this specification the term "irreversible bond" means a bond, the dissociation constant of which is lower than the dissociation constant of an immunochemical bond. In particular the bonds between the solid phase and the second antibody have a lower dissociation constant than the dissociation constants of the immunochemical bonds which bind the first and second antibodies to the ligand molecules.

The sequence and combination of the mixing and incubation of the components of the assay has an effect upon the sensitivity of the assay and upon the ease with which the assay may be performed. Preferably, the mixture is formed by mixing the separate components in one step. In this way the separate components are each placed in competition contemporaneously and an effective competitive reaction results. From a practical point of view this technique has some limitations. In an alternative preferred method the mixture is formed by:

forming a mixture of the sample solution and the ligand molecule and mixing the said mixture with a mixture formed between the first antibody and the second antibody. In this way the antigenic components of the assay (the sample and the ligand molecule) may be prepared but will not react with each other and the antibody components of the assay (the first and second antibodies) may be prepared but will not react with each other; reaction only occurring when the antigenic and antibody components are mixed.

The solid phase may be washed at appropriate stages of the assay to clear away species which are not bound to the solid phase.

One or more of the first, second and labelled antibodies may be immunoglobulin enriched fractions of antisera to the relevant antigens or monoclonal antibodies to the relevant antigens.

The labelled antibody is preferably capable of producing a visible signal with or without a suitable substrate. More preferably the labelled antibody is labelled with an enzyme, a fluorphor or a chemiluminescent radical. For example there may be used horse radish peroxidase, alkaline phosphatase, β-galactosidase or glucose oxidase. Most preferred is an antibody labelled with horse radish peroxidase.

The solid phase support may be a microtitration plate such as a microtest plate, or a microtitre plate, plastic or glass tubes, balls or beads, latex particles, a microscope slide, particulate cellulose, preferably microcrystalline cellulose, agarose, sepharose, sephacryl, a polyacrylamide particulate gel, a silica gel, an alumina, a zeolite, or a fibrous material for example cellulose in the form of a filter paper etc.

Preferably the solid phase support is a microtitration plate.

The binding of the second antibody to the solid phase may be achieved by any known means for example chemically or by means of a polypeptide for example anti-immunoglobulin antibody, protein A, or killed or fixed *Staphylococcus aureus*.

The assay may be used in a method for determining the fertile period of the menstrual cycle in which the assay is used to monitor the relative concentrations of oestrone-3-glucuronide and pregnanediol-3-glucuronide in urine. In this preferred use of the assay the ligand molecule may comprise at least one molecule of oestrone-3-glucuronide and at least one molecule of pregnanediol-3-glucuronide irreversibly bound through a bridge support molecule.

Preferably the ligand molecule is of the formula

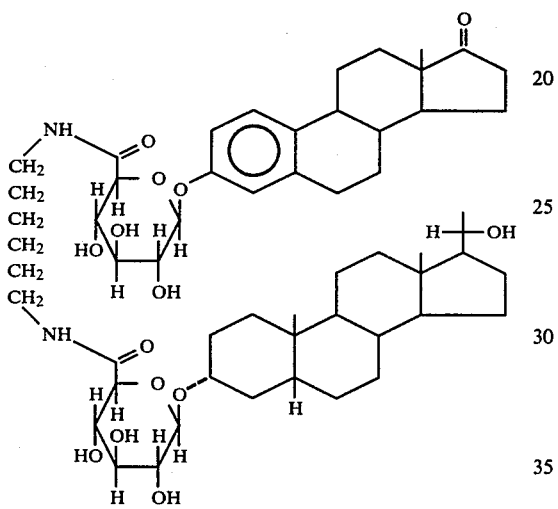

The present invention also provides for a reagent kit for performing the assay of the present invention or the method described immediately above. In this connection there is provided a reagent kit comprising separately, the first antibody, the second antibody and the ligand molecule. There is also provided a reagent kit comprising a mixture of the first antibody and the second antibody and separately the ligand molecule.

The invention further provides a ligand molecule comprising two, different antigenic radicals irreversibly bound through a bridging support molecule, the bridging support molecule being a divalent radical derived from an organic compound having two reactive functional groups. The divalent radical may be alkyl having 2 to 10 carbon atoms, alkene having 2 to 10 carbon atoms, alkyne having 2 to 10 carbon atoms or phenyl dialkyl. Preferably the divalent radical is derived from a compound of the general formula

wherein R is —NH₂, —halogen or —O—CO-alkyl and n is 2 to 10. Preferably R is —NH₂. Preferably n is 6. Most preferred is a ligand molecule of the following formula:

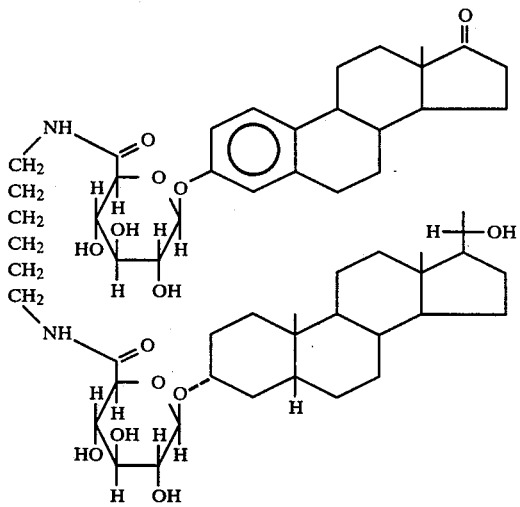

The reagent system of the present invention overcomes the limitations inherent in the system described in British patent specification No. 2029011B by replacing the proteinaceous support molecule comprising part of the bifunctional ligand with a simple bridging support molecule derived from an organic compound having two reactive functional groups. The relevant steroid metabolites (in the case of the specific embodiment to be described, oestrone-3-glucuronide and pregnanediol-3-glucuronide) may be attached chemically to such a bridging support molecule to form a ligand molecule hereinafter referred to as mixed steroid antigen or MSA. An example of a suitable bridging support molecule is an alkyl diamine e.g. 1,6-diaminohexane. Mixed steroid antigens using such synthetic support molecules exhibit a greatly reduced tendency to form multivalent immunocomplexes and have negligible immunological affinity to antibodies present in the system as impurities.

The method of the present invention takes into account the generally lower level of one of the antigenic solutes (in the case of the specific embodiment oestrone-3-glucuronide). It has been found necessary to increase proportionately the sensitivity of the method for the antigenic solute which is in lower concentration. This has been achieved by allowing for a truly competitive reaction between the MSA and the antigenic solute for complexing with the antibody to the antigenic solute in question. In the method described in British patent specification No. 2029011B a dissociation of the immunocomplex formed between the antibody and the MSA is necessary before true competition can begin.

It has been found that a more sensitive assay results when the components of the reagent system are added such that the MSA has to compete with the sample for binding to either antibody.

In the specific embodiment to be described the above-mentioned reagent system and method are used to determine the day or days in the menstrual cycle when the concentration ratio of oestrone-3-glucuronide to pregnanediol-3-glucuronide in the urine becomes elevated. Testing of successive daily urines throughout a menstrual cycle would therefore indicate the onset, the duration and the end of the fertile period. In addition, since the ratio reaches a peak value around the day of ovulation, observation of a peak would indicate the time of maximal fertility.

Figure 2:
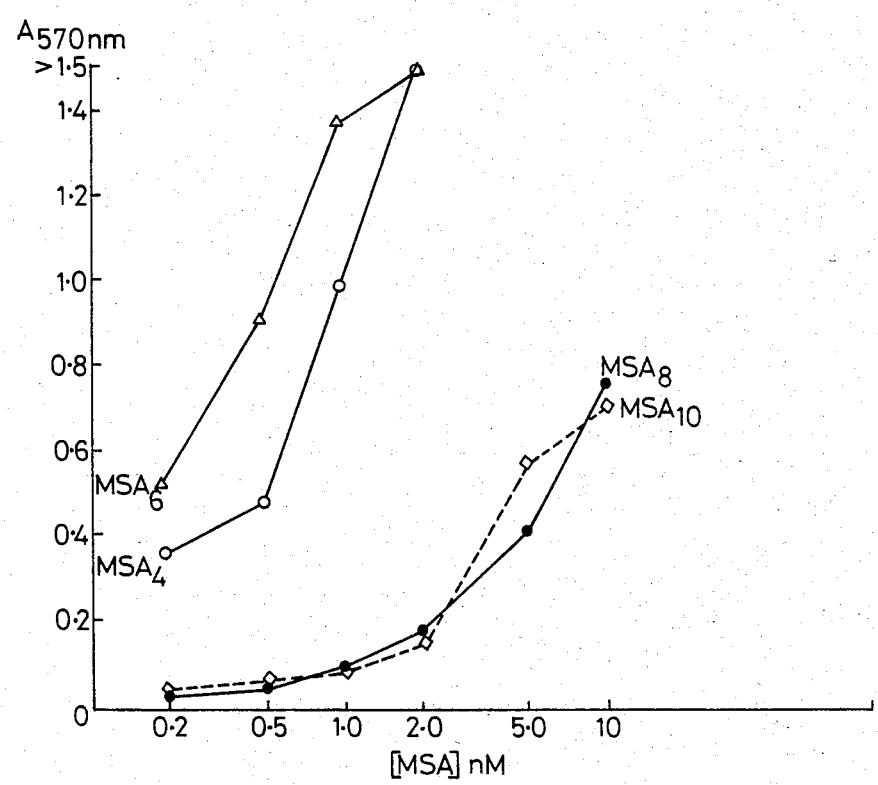
Figure 3:
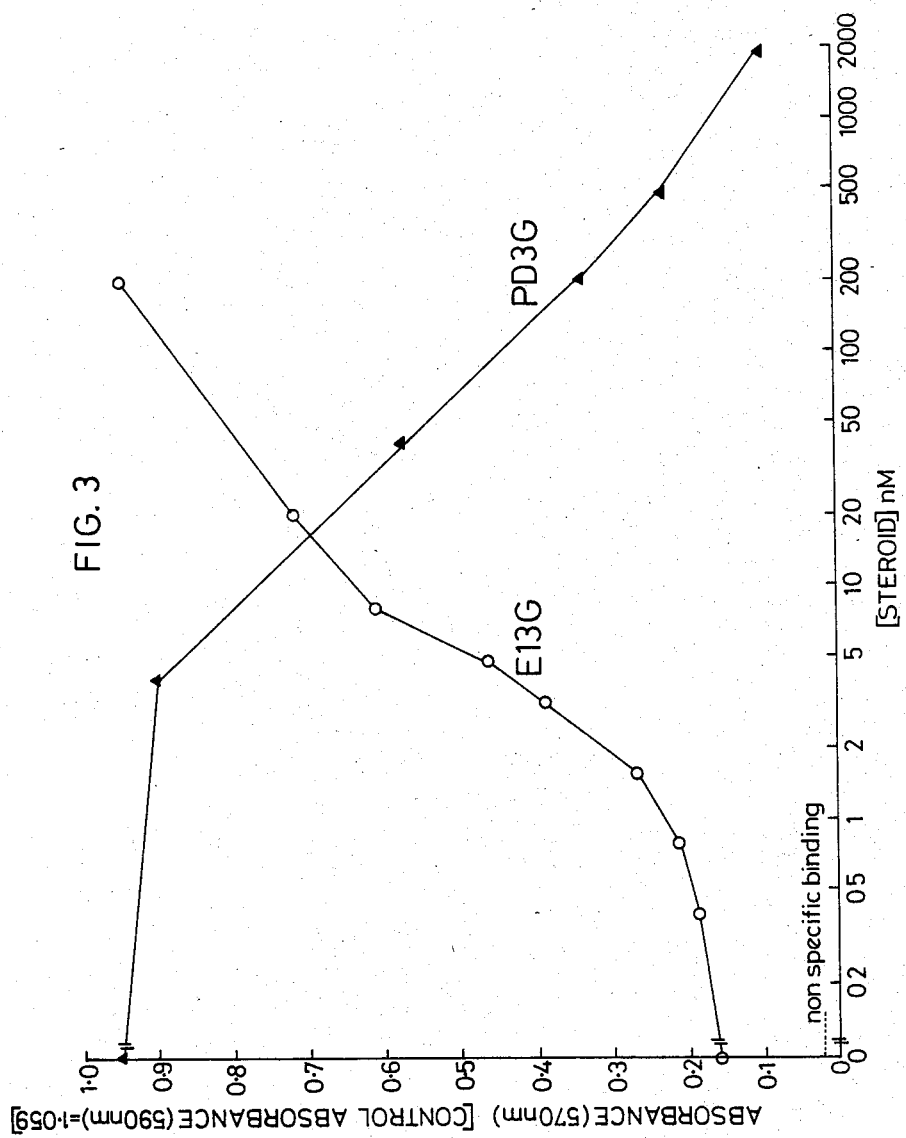
Figure 4:
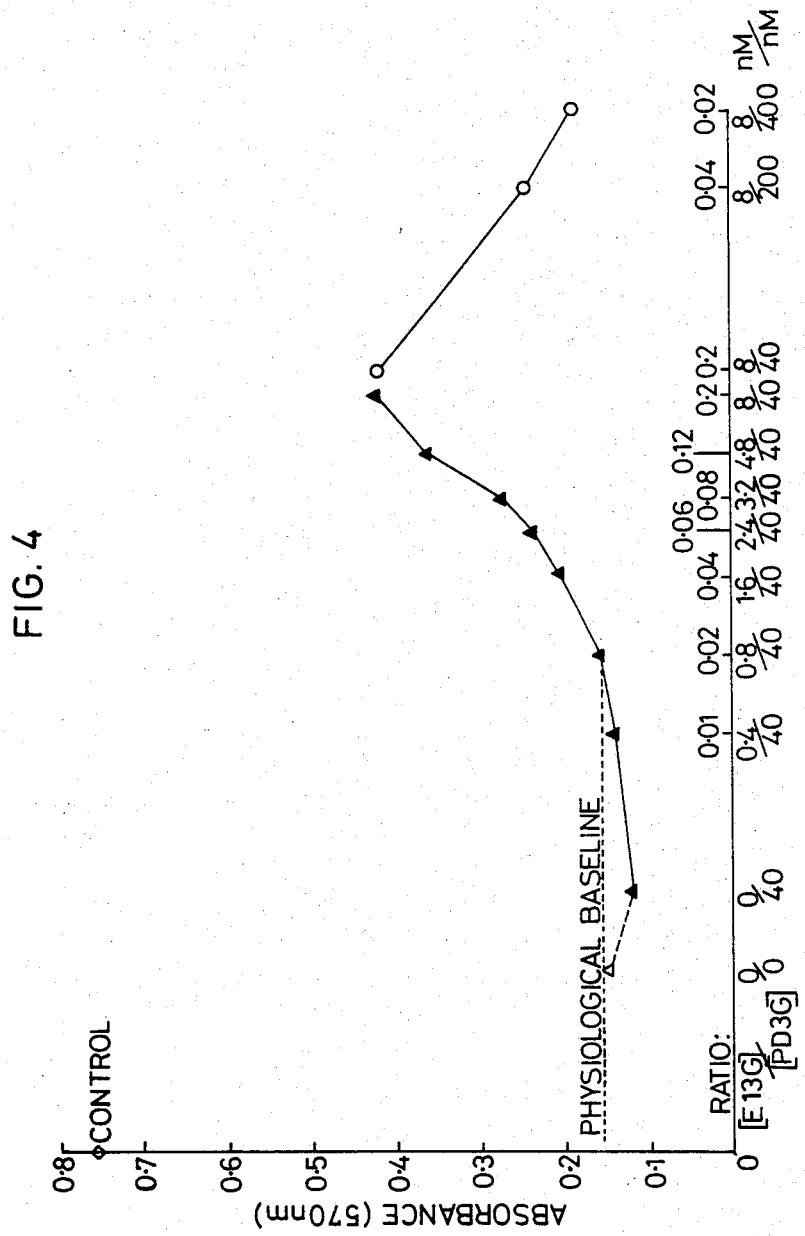

An embodiment of the reagent system and the dual analyte assay is now described with reference to the accompanying drawings in which:

FIG. 1 is a schematic diagram showing the operation of an embodiment of the dual analyte assay under various extremes of concentration of two analytes, E13G and PD3G, FIG. 2 is a graph showing the effect of varying the length of the bridging support molecule of a ligand upon the binding of a labelled antibody (anti-E13G-peroxidase, AEP) to a solid phase antibody (solid phase anti-PD3G, SPAP), FIG. 3 is a graph showing the dose-response curves of the dual analyte assay to E13G and PD3G, FIG. 4 is a graph showing the dose response curve of the dual analyte under conditions of a simulated menstrual cycle, FIG. 5 is a graph showing the results of the dual analyte assay for a typical menstrual cycle, FIG. 6 is a bar graph summarizing the results obtained when the dual analyte assay was used to measure daily urine samples from 17 women each over their complete menstrual cycle.

An embodiment of the reagent system and a dual analyte assay is schematically described in FIG. 1. In the drawing the following symbols are used:

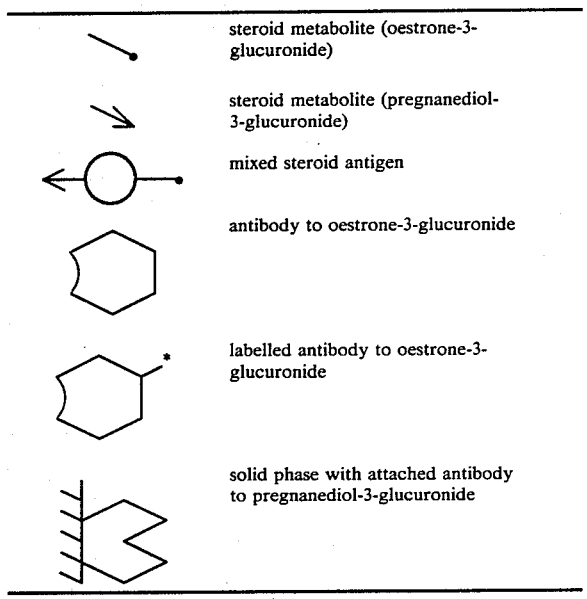

Four extremes in the concentrations of the two antigenic solutes are shown.

(i) Oestrone-3-glucuronide (E13G) concentration high. Pregnanediol-3-glucuronide (PD3G) concentration low.

This represents the situation during the periovultary phase of the menstrual cycle, and therefore the situation in which we are especially interested. A sample of urine is taken out, diluted as necessary, it is added to a buffer solution containing a mixed steroid antigen having antigenic determinants to both oestrone-3-glucuronide and pregnanediol-3-glucuronide. This mixture of antigens is then added to an antibody to oestrone-3-glucuronide in solution and an antibody to pregnanediol-3-glucuronide attached to a solid phase. The antigens present upon the mixed steroid antigen compete with the antigenic analytes for binding to their respective antibodies. In the present case the relatively high concentration of oestrone-3-glucuronide in the sample results in a large proportion of the antibody to oestrone-3-glucuronide becoming bound to the analyte, leaving mixed steroid antigen attached to the solid phase having free antigen corresponding to oestrone-3-glucuronide. An optional buffer wash, and incubation with a labelled antibody to oestrone-3-glucuronide results in the labelled antibody becoming associated with the solid phase where it may be detected.

(ii) Oestrone-3-glucuronide (E13G) concentration low. Pregnanediol-3-glucuronide (PD3G) concentration low.

This represents the situation in the early follicular phase of the menstrual cycle. The test procedure is as above but as indicated in the drawing no signal is produced as insufficient urinary oestrone-3-glucuronide is present to compete to a significant extent with the mixed steroid antigen. As a result the majority of oestrone-3-glucuronide moieties on the mixed steroid antigen finally bound to the solid phase are associated with unlabelled antibody to oestrone-3-glucuronide which prevents labelled antibody to oestrone-3-glucuronide from associating with mixed steroid antigen, and hence from producing a signal.

(iii) Oestrone-3-glucuronide (E13G) concentration high. Pregnanediol-3-glucuronide (PD3G) concentration high.

This represents the situation in the mid luteal phase of the menstrual cycle. The test procedure is as above but as indicated in the drawing no signal is produced as the mixed steroid antigen is not able to associate to a significant extent with either the pregnanediol-3-glucuronide antibody or the oestrone-3-glucuronide antibody due to the high concentration of the steroid metabolites in the urine. As a result the majority of the mixed steroid antigen molecules are not bound to the solid phase and are washed off before incubation with labelled antibody.

(iv) Oestrone-3-glucuronide (E13G) concentration low. Pregnanediol-3-glucuronide (PD3G) concentration high.

In this situation the relatively high concentration of pregnanediol-3-glucuronide to a significant extent prevents the association of the mixed steroid antigen with the solid phase and hence no signal is observed.

In the following we describe the preparation and characterisation of the various components of the reagent system.

MATERIALS AND METHODS

Unless specified otherwise, all chemicals and solvents were obtained from BDH Chemicals Ltd., Poole, Dorset, U.K. All buffers were made up in distilled water.

BARBITONE BUFFER

Sodium Barbitone was made up to a final concentration of 0.07M together with 0.1% (w/v) sodium azide. The pH of this solution was adjusted to 8.4 with concentrated hydrochloric acid before making up to the final volume.

BLOCKING BUFFER

Blocking buffer contained 0.1M sodium chloride and 0.1M phosphate (prepared from 11.53 g/l anhydrous disodium hydrogen phosphate and 2.25 g/l anhydrous sodium di-hydrogen phosphate). Bovine serum albumin (Grade V, Sigma Chemical Co. Fancy Road, Poole, Dorset, U.K.) was dissolved in this solution to a concentration of 5% (w/v).

WASHING BUFFER

A solution was prepared containing 0.1M sodium chloride, 0.01M ethylenediamine tetra-acetic acid and 0.01M phosphate (consisting of 1.153 g/l anhydrous disodium hydrogen phosphate and 0.225 g/l sodium di-hydrogen phosphate). To each liter of this solution was added 10 ml of n-butanol and 0.2 ml of Tween-20. The resulting washing buffer was well shaken and adjusted to pH 7.5 with concentrated hydrochloric acid.

TRIS-HCL BUFFER

A solution containing tris 0.02M (Trizma base, Sigma Chemical Co, Fancy Road, Poole, Dorset, U.K.) and 0.5M sodium chloride was prepared and adjusted to pH 7.4 with concentrated hydrochloric acid.

ESPE BUFFER

A solution was prepared containing 0.1M sodium chloride, 0.01M EDTA and 0.1M phosphate (as 11.53 g/l anhydrous di-sodium hydrogen phosphate and 2.25 g/l sodium di-hydrogen phosphate), the pH was adjusted to 7.0 with concentrated hydrochloric acid. To each liter of solution was added 175 ml of absolute ethanol (A.R. grade) and 0.2 ml of Tween-20.

PRIMARY BUFFER

Primary buffer was prepared by dissolving bovine serum albumin (Grade V, Sigma Chemical Co., Fancy Road, Poole, Dorset, U.K.) in ESPE buffer to give a 2% (w/v) solution.

SECONDARY BUFFER

Secondary buffer was prepared by dissolving the same grade bovine serum albumin in ESPE buffer to a concentration of 0.2% (w/v).

SUBSTRATE SOLUTION A

Substrate solution A consisted of 0.01M dimethyl aminobenzoic acid (Aldrich Chemical Co., The Old Brickyard, New Road, Gillingham, Dorset, U.K.), 0.1M ammonium sulphate, 0.01M EDTA and 0.02M phosphate (as 2.307 g/l anhydrous di-sodium hydrogen phosphate and 0.45 g/l anhydrous sodium di-hydrogen phosphate). The pH of this solution was adjusted to 6.0 with 2M sodium hydroxide. Finally, 10 ml of n-butanol was added per liter of solution.

SUBSTRATE SOLUTION B

Substrate solution consisted of 0.02M 3-methyl-2-benzothiazolinine hydrazone hydrochloride (Aldrich Chemical Co. Ltd.) in water.

SUBSTRATE SOLUTION C

Substrate solution C was prepared by diluting 30% hydrogen peroxide in water to give a 1M solution.

PROTEIN A DESORBING BUFFER

Protein A desorbing buffer consisted of 0.15M sodium chloride and 0.58% (v/v) acetic acid.

CON-A DESORBING BUFFER

Con-A desorbing buffer consisted of 0.5M $\alpha$-methyl mannoside (Sigma Chemical Co.) in Tris/HCl buffer.

ACETATE BUFFER

This consisted of 0.1M sodium acetate, 0.1M sodium chloride and was adjusted to pH 4.5 with hydrochloric acid.

PHOSPHATE BUFFERED SALINE

Phosphate buffered saline contained 0.1M sodium chloride and 0.1M phosphate (prepared from 11.53 g/l anhydrous di-sodium hydrogen phosphate and 2.25 g/l anhydrous sodium di-hydrogen phosphate). The buffer was adjusted to pH 7.5.

PREPARATION OF VARIOUS MIXED STEROID ANTIGEN (MSA) COMPOUNDS

The following MSA's have been prepared:
1-[pregnanediol-3-glucuronamido], 4-[oestrone-3-glucuronamido]-butane (or PD3G-1, 4(DAB)-E13G)
1-[pregnanediol-3-glucuronamido], 6-[oestrone-3-glucuronamido]-hexane (or PD3G-1, 6(DAH)-E13G)
1-[pregnanediol-3-glucuronamido], 8-[oestrone-3-glucuronamido]-octane (or PD3G-1, B(DAO)-E13G)
1-[pregnanediol-3-glucuronamido], 10-[oestrone-3-glucurona-mido]-decane (or PD3G-1, 10(DAD)-E13G), (hereafter abbreviated to MSA$_4$, MSA$_6$, MSA$_8$ and MSA$_{10}$ respectively).

The following alkyl diamines were mono-substituted with E13G using the mixed anhydride method described by Samarajeewa, P and Kellie A. E. (1975) Biochem. J 151 369–376
1,4-diaminobutane
1,6-diaminohexane
1,8-diaminooctane
1,10-diaminodecane A simplified work up procedure was developed based on the use of reverse phase sep-pak $C_{18}$ cartridges, (Waters Ltd., 324 Chester Road, Hartford, Northwich, Cheshire, U.K.).

The following describes the general method for preparing mono substituted steroid glucuronyl alkyl diamines:
E13G: (10 $\mu$mol)+H$^3$E13G ($10^6$dpm)
dry dimethylformamide (DMF): (400 $\mu$l)
dry t-N-butylamine: (7.5 $\mu$l)
isobutylchloroformate: (4.5 $\mu$l)
stir, 30 min, $-10°$ C.
add to 150 $\mu$mol alkyl diamine in 600 $\mu$l DMF
stir, 10 min, 0° C., leave 18 h, 4° C.
add 20 ml water, leave 18 h, 4° C.
add 20 ml water, apply to $C_{18}$ cartridge
wash with 10 ml 50% methanol in water
wash with 10 ml water
wash with 10 ml 30% MeOH containing 1% acetic acid
elute cartridge with 50 ml 50% MeOH containing 1% acetic acid
dilute eluent to 100 ml with water, apply to fresh $C_{18}$ cartridge
wash with 10 ml 0.1M sodium carbonate
wash with 10 ml water
elute with 50 ml MeOH, take to dryness.

Impurities were largely removed by washing cartridges with methanolic solutions of differential polarity and pH. T.L.C. of final residues revealed fairly pure product in each case. Yields ranged from 31% to 43%. These intermediates were taken to the next step without further purification.

PD3G was coupled to the following E13G monosubstituted alkyl diamine derivatives by the mixed anhydride reaction;
E13G-1,4(DAB)
E13G-1,6(DAH)
E13G-1,8(DAO)
E13G-1,10(DAD)
Again sep-pak $C_{18}$ cartridges were used to facilitate product isolation.

The following describes the general method for coupling second steroid glucuronide to mono-substituted steroid glucuronyl alkyl diamines.
PD3G: (5 μmol)
dry DMF: (200 μl)
t-N-butyl amine: (4 μl)
isobutylchloroformate: (3 μl)
stir, 30 min, −10° C.
add to 4 μmol E13G-alkyl diamine in 500 μl dry DMF
stir, 1 h, 0° C. leave 18 h, 4° C.
add 20 ml water
leave 18 h, 4° C.
apply to $C_{18}$ cartridge
wash with 10 ml water
wash with 10 ml of 50% methanol in 0.1M sodium carbonate
wash with 10 ml of 50% methanol containing 1% acetic acid
wash with 10 ml of water
elute with 10 ml methanol
take to dryness
purify by HPLC Yield of product in the final methanolic eluent ranged from 44% to 81%. T.L.C. indicated only slight traces of impurities. Rf values were in the expected order with polarity increasing with decreasing bridge length. The four new MSAs were further purified by high pressure liquid chromatography.

Cekan and de Gomez Anal. Letts. 12, pp. 589–602 (1979) have reported that the chemical purity of a radioligand can be assessed by examining successive fractions of a chromatogram of the radioligand for specific activity. If the specific activity of each fraction around the peak remains constant then this is indicative of purity. Conversely changes in specific activity of successive fractions would indicate the presence of a co-eluting contaminant.

The specific activities of $MSA_6$ were estimated for the peak fraction and two fractions either side of a peak in an HPLC chromatogram. Radioactivity in each fraction was determined by counting 10 μl in duplicate. The mass of MSA in each fraction was determined by RIA (radioimmunoassay), both by an E13G RIA system and a PD3G RIA system. Since in an RIA system parallelism of an analyte with a standard is another indicator of purity, the assays were performed over a range of fraction dilutions. Each fraction was assessed at 5 (doubling) dilutions, each performed in duplicate.

The results of this study are presented in Table 1. The standard deviations around the mean of the 5 determinations on each fraction indicate a fairly consistent result independent of fraction dilution, with the exception of fraction +2. The specific activity of fractions −2, −1, 0 and +1 remained constant within the calculated error limits. Fraction +2 had a significantly different specific activity and was therefore excluded from the preparation.

What was striking about the results was the very close agreement in specific activities calculated by the two different RIAs. The mean specific activity of fractions −2, −1, 0 and +1 (determined by both RIAs) was 21.5±3.9 cpm/pmol. It was concluded that the MSA used in subsequent immunochemical work was pure.

TABLE 1

| Specific activities of $MSA_6$ in peak fractions from HPLC chromatogram | | | | | | |
|---|---|---|---|---|---|---|
| HPLC FRACTION NO. | | 30 | 31 | 32 | 33 | 34 |
| FRACTION RELATIVE TO PEAK | | −2 | −1 | 0 | +1 | +2 |
| RADIOACTIVITY cpm/10 μl | | 759 | 4136 | 11326 | 3716 | 1638 |
| RANGE OF DILUTION FACTORS × $10^{-3}$ | | 1–16 | 5–80 | 10–160 | 5–80 | 2–32 |
| CONCENTRATION OF MSA BY RIA μM | [E13G] | 3.0 ± 0.3 | 15.1 ± 3.1 | 56 ± 7 | 19.2 ± 3.8 | 3.4 ± 0.9 |
| | [PD3G] | 3.1 ± 0.6 | 21.5 ± 7.2 | 60 ± 10 | 22.1 ± 6.5 | 5.4 ± 1.4 |
| SPECIFIC ACTIVITY OF MSA cpm/pmol | E13G RIA | 26 ± 3 | 27 ± 6 | 20 ± 3 | 19 ± 4 | 49 ± 13 |
| | PD3G RIA | 25 ± 4 | 19 ± 6 | 19 ± 3 | 17 ± 5 | 31 ± 8 |

PREPARATION OF ANTI-PG3G SOLID PHASE (SPAP)

Rabbit antiserum was supplied by the Courtauld Institute of Biochemistry Cleveland Street, London, W.1., (preparation PG01/Z00, bleed VIII) and had been raised against an immunogen prepared by the covalent attachment of PD3G through its carboxyl to the ε-amino-lysyl residues of bovine serum albumin as described by Samarajeewa, Cooley and Kellie (1979). [The radioimmunoassay of prenanediol-3α-glucuronide, Journal of Steroid Biochemistry 11 1165–1171]

An IgG fraction of this antiserum was prepared as follows. To remove carrier specific antibodies, 0.4 ml of blocking buffer was added to 10 ml of anti-PD3G antiserum. The mixture was incubated at 37° C. for 3 hours then left at 4° C. overnight. The resulting precipitate was removed by centrifugation and the pellet washed twice with 10 ml of phosphate buffered saline. The combined supernatant (30.5 ml) was chilled to 4° C. and a chilled solution of rivanol (6,9-diamino-2-ethoxy acridine lactate, 0.16 g/19.5 ml) gradually added with stirring. The mixture was adjusted to pH 8.4 with 2M sodium hydroxide. Stirring was continued at 4° C. for 30 minutes when 25 mg of powdered charcoal (Norit A) was added.

The suspension was centrifuged and the resulting supernatant passed through a 0.2 μm disposable filter cartridge. (Schleicher & Schull GmbH Postfach 4.D-

3354 Dassel, W. Germany). Further purification involved protein A-sepharose affinity chromatography.

A small column containing protein A-sepharose (Sigma Chemical Co. Ltd.) was packed in phosphate buffered saline to give a bed volume of 15×1 cm diameter. The previous filtrate containing anti-PD3G was applied to the top of the column under gravity, followed by 200 ml of phosphate buffered saline to remove any non-bound protein from the gel.

Protein-A desorbing buffer was then applied to the column in the reverse direction and the eluent collected to a total of 70 ml. The pH of this eluted protein fraction was adjusted to 7.0 with 2M sodium hydroxide. Absorbance measurements on this solution indicated that 62 mg of enriched IgG had been prepared. The anti-PD3G solution was stored at −70° C. until required.

Microtest plates (Nunc, Immunoplate I, Gibco Europe Ltd., P.O. Box 35, Washington Road, Paisley, U.K.), were used as the solid phase to prepare SPAP. Anti-PD3G was passively adsorbed to the wells of a plate by incubating a solution of the antibody in the wells.

A solution of anti-PD3G in barbitone buffer was made up to give approximately 3 $\mu$g/ml of protein. This concentration was determined by experiment to give high adsorption of protein to the well surface on the one hand whilst being relatively economical on antibody solution on the other.

Microtest plates were coated with antibody by pipetting 200 $\mu$l of the anti-PD3G solution into the wells using a 12-channel pipette (Titertek, Flow Laboratories Ltd., P.O. Box 17, 2nd Avenue, Irvine, Ayrshire, U.K.). The wells were sealed using plastic film and left at room temperature for 24 hours. At the end of this time the contents of the wells were aspirated and the wells flooded with blocking buffer. The wells were again sealed and left at room temperature for 18 hours.

Finally, the contents of the wells were aspirated and the wells washed four times with distilled water. Each plate was inverted and tapped several times on a bench surface coated with tissue paper. The thin film of water remaining in the wells was allowed to evaporate at room temperature for 2 hours. The wells were then sealed with plastic film and stored at −18° C. until required.

PURIFICATION OF ANTI-E13G ANTIBODIES

Rabbit anti-E13G sera were supplied by the Courtauld Institute of Biochemistry, Cleveland Street, London W1 and were prepared as described by Samarajeewa and Kellie (1975) (Samarajeewa P. and Kellie A. E. (1975). The radio-immunoassay of steroid glucuronides; the oestrogen C-3 glucuronides as haptens Biochemical Journal 151 369–376). The primary reaction of the dual analyte assay required diluted anti-E13G which was used without further purification. However, in order to prepare peroxidase labelled anti-E13G, 10 ml of an antiserum was fractionated by treatment with bovine serum albumin, rivanol and then by affinity chromatography using protein A-sepharose, in an identical manner to that described during the preparation of anti-PD3G solid phase. By this method 70 mg of an IgG enriched fraction of anti-E13G was obtained.

PURIFICATION OF HORSE RADISH PEROXIDASE (HRP)

Horse radish peroxidase (Type VI, Sigma Chemical Co. Ltd., E.C. No. 1.11.1.7) was purified by affinity chromotagraphy using concanavalin A-sepharose (Sigma Chemical Co. Ltd.). The gel was equilibrated in tris/HCl buffer and packed in a column to give a bed of 27×1 cm diameter. 80 mg of the peroxidase was dissolved in 5 ml of tris-HCl buffer and applied to the column, the column was eluted with 25 ml of tris/HCl under gravity. The elution profile was monitored spectrophotometrically at 280 nm and at 403 nm.

The elution was continued with Con-A desorbing buffer and after a further 5 ml had been eluted, fractions were obtained with A403/A280 values of between 3.1 and 3.5. These fractions were collected and pooled to give a total of 18 ml, containing an estimated 64 mg of peroxidase. The peroxidase was further purified by gel filtration using sephacryl S-200 (Pharmacia Ltd., Prince Regent Road, Hounslow, Middx. U.K.). The sephacryl gel was equilibrated in tris/HCl buffer and packed in a column to produce a bed of dimensions 72×3.2 cm diameter. The peroxidase solution was applied to the column and the column eluted with tris/HCl with a 1.2 m hydrostatic head. The column was monitored at 280 mm and 403 mm wavelengths and after 240 ml eluent had been collected, fractions were observed with A403/A280 values of approximately 3.3. These fractions were pooled and totalled 63 ml, representing some 57 mg of peroxidase. A 56 ml portion of this solution was concentrated to a final volume of 5 ml and dialysed against phosphate buffered saline by means of a microultrafiltration unit (Model 8MC, Amicon, Ltd., Upper Mill, Stonehouse, Gloucester, U.K.).

PREPARATION OF ANTI-E13G -PEROXIDASE (AEP)

Purified peroxidase was covalently attached to purified anti-E13G using the heterobifunctional reagent: N-succinimidyl 3-(2-pyridyldithio) propionate (SPDP; Pharmacia Ltd.). The advantage of using this reagent was that the formation of homoconjugates between enzyme and enzyme and between antibody and antibody may be avoided. The reaction scheme followed has been well described (Pharmacia Ltd., product literature: "SPDP heterobifunctional reagent", also Carlsson, J., Drevin, H. Axen, R. (1978) Biochem. J. 173 723–737).

Both enzyme and antibody were activated by separate reactions with SPDP. Then one component, in this case the derivatized peroxidase, was reduced with dithiothreitol. The derivatized peroxidase, bearing a free thio group, was then allowed to react with the derivatized antibody resulting in the formation of a dithiol bridge between antibody and enzyme. The liberation of pyridine-2-thione by reducing either intermediate was used to estimate the degree of substitution spectrophotometrically.

A solution of purified anti-E13G (31 ml) containing 36 mg of protein was dialysed against phosphate buffered saline. A 50-fold molar excess of SPDP in 0.5 ml ethanol was slowly added to the stirred antibody solution which was maintained at 23° C. for 30 minutes. The mixture was then subjected to gel filtration by applying 2.5 ml aliquots to a total of 16 sephadex G-25 PD10 pre-packed columns (Pharmacia Ltd.). The columns had been previously equilibrated in phosphate buffered saline. Derivatized anti-E13G was eluted from each column with 3.5 ml of the same buffer, to give a total of 56 ml. The substitution of anti-E13G was estimated to be 11 2-pyridyl disulphide groups per molecule of IgG.

In parallel the activation of purified peroxidase was carried out by adding a solution of SPDP (32 μmol) in 0.8 ml ethanol to a stirred solution of peroxidase (51 mg/5 ml) and maintained at 23° C. for 30 minutes. After this time the reaction mixture was dialysed against 25 ml phosphate buffered saline in a microultra filtration unit.

The derivatized peroxidase was subjected to gel filtration using five sephadex G25 PD10 columns (2.5 ml per column) which had been equilibrated in acetate buffer. Protein was eluted with 3.5 ml of buffer per column to give a total of 17.5 ml. Free thiol groups were generated by treating this peroxidase solution with 135 mg of dithiothreitol and the mixture stirred at 23° C. for 20 minutes.

The reaction mixture was subject to gel filtration using seven sephadex G25 PD10 cartridges which had been equilibrated with phosphate buffered saline. A total of 24.5 ml of protein solution was collected by eluting each column with 3.5 ml buffer. This was concentrated using a microultrafiltration unit to a final volume of 5.6 ml and dialysed against 25 ml phosphate buffered saline. The number of pyridine-2-thione groups liberated per molecule of peroxidase was estimated to be 1.7.

The modified peroxidase solution (5.6 ml) was mixed with the derivatized anti-E13G solution (53 ml) and stirred for 24 hours at 23° C. It was estimated that 1.6 molecules of pyridine-2-thione were released per molecule of IgG during the course of the reaction.

The resulting conjugate was purified from unconjugated peroxidase and unconjugated anti-E13G by a double affinity chromatography procedure as follows. The reaction mixture was applied to the regenerated concanavaline A-sepharose column and eluted with 136 ml of tris/HCl buffer. The regenerated protein A-sepharose column was then connected in series to the outlet of the previous column and elution was continued using Con-A desorbing buffer, until a further 60 ml had been collected.

The concanavalin A-sepharose column was disconnected and elution continued through the protein A-sepharose column using tris/HCl buffer, for a further 100 ml. The flow through this column was then reversed and the eluent replaced with protein A desorbing buffer. The elution of the conjugate was complete after 50 ml had been collected. AEP containing fractions having an A403/A280 value of approximately 0.6 were pooled, neutralized with dilute sodium hydroxide and made up to 50 ml. Finally the AEP solution was aliquotted into 0.5 ml portions, snap frozen in liquid nitrogen and stored at −70° C.

The yield of antibody incorporated into AEP was 68% and the molar incorporation ratio of peroxidase to anti-E13G from the A402/A280 value to be 1.6. The optimal working dilution of the AEP was determined by experiment. The described preparation had a useful working range of between 1000 and 5000-fold dilution. For the dual analyte assay it was preferable to dilute the AEP preparation 1500-fold to give a working concentration of conjugate of approximately 2 nM i.e. 0.4 pmol per microtest well.

We now describe in detail a protocol for performing a dual analyte assay of the present invention. This protocol describes an optimised method for determining the changes in concentration of E13G relative to the concentration of PD3G in menstrual cycle urine.

A. PRIMARY REACTION

1. Anti-PD3G coated microtest plates were removed from −18° C. storage and allowed to equilibrate at room temperature, before removing the protective plastic film. On each plate of 96 wells 4 wells were designated controls and 4 wells were designated non-specific binding wells.

2. Anti-E13G antiserum was diluted in primary buffer by a factor of 3750, to a volume of 10 ml for each plate to be used in the assay. To every well of the plate except control wells, 100 μl aliquots of this solution of anti-E13G was pipetted. To the control wells, 100 μl aliquots of primary buffer was pipetted.

3. Initial dilutions of urine or standard samples were made either in test tubes or 12-channel reservoirs. (Dynatech Laboratories, Daux Road, Billingshurst, Sussex, U.K.). Use of the latter together with a 12-channel pipette enabled rapid transfer of reagents and sample into the microtest plates.

Dilutions were made in primary buffer, a range of dilution factors was tried, but typically 80 μl of urine or standard solution was diluted to 500 μl. To the diluted sample was added 500 μl of a solution containing 4.8 nM $MSA_6$ and 40 nM PD3G in primary buffer. The mixtures were throughly mixed by vortexing test tubes or rocking the reagent reservoirs at least 20 times.

4. The primary reaction was initiated by adding 100 μl aliquots of the MSA and sample mixture to the SPAP wells, containing the anti-E13G solution. This addition was made to all wells except the non specific binding wells to which was added 100 μl of primary buffer. The final concentration of MSA in the sample and control wells was 1.2 nM; the final dilution of anti-E13G in the sample and non-specific binding wells was 7500-fold. The addition was preferably performed within one minute. The wells were covered with plastic film or a plastic lid and shaken for 1 hour at room temperature on a flat bed orbital shaker. A shaking speed of 240 revs/minute, with an orbit of 1.5 cm diameter was preferred.

5. At the end of the primary reaction, the plates were removed from the shaker and washed with washing buffer, preferably using a 12-channel Nunc-Immunowash device. (Flow Labs Ltd.). This device allowed one row of 12 wells to be washed simultaneously. The procedure followed was thus: each row in turn was aspirated then flooded with washing buffer. After the final row had been treated, this washing cycle was repeated three more times. Finally, the contents of the wells were aspirated and the whole plate inverted and given several sharp taps against a bench coated with a wad of tissue paper.

B. SECONDARY REACTION

A stock solution of anti-E13G-peroxidase (AEP) conjugate was thawed and diluted with secondary buffer 1500-fold. (2 nM). Aliquots of 200 μl of this solution were pipetted into the microtitre plate immediately after the previous steps. The plate was similarly covered and shaken as before for 1 hour at room temperature.

The wells were washed in similar fashion as after the primary reaction, with the exception that during the 4th washing cycle, the washing buffer was left in the wells for a total of 10 minutes before aspirating and tapping dry.

C. TERTIARY REACTION

For each plate used, the following volumes of substrate solutions were mixed, no more than 30 minutes before the start of the tertiary reaction.
Substrate Solution A: 20 ml
Substrate Solution B: 200 µl
Substrate Solution C: 20 µl
200 µl of this mixture was pipetted into all the wells and the plate again covered and shaken as before except that the reaction time was only 15 minutes.

At the end of this time, the colour development in each well was measured using a Microelisa auto reader (Dynatech Laboratories Ltd). Since all 96 wells could be read within about 100 seconds, it was not necessary to stop the enzyme reaction. The wavelength filter in the test beam of the instrument was set to 570 nm and the wavelength of the reference beam set to 405 nm. The instrument had been zeroed immediately prior to use against 200 µl of the substrate mixture which had been pipetted into a untreated microtest plate.

Results were expressed as mean absorbance (A 570 nm) readings for replicated samples and usually transformed as a percentage of the mean $A_{570\,nm}$ of the control wells.

In menstrual cycle urine E13G ranges from 10 to 400 nM and for the purposes of detecting a pre-ovulatory E13G surge the critical range is 20 to 100 nM. PD3G has a normal range of 100 to 50,000 nM in menstrual cycle urine and for the purposes of detecting the end of the fertile period the critical range is 1000 to 4000 nM.

The assay system was optimised to be simultaneously responsive to concentrations of both steroids likely to be found in menstrual cycle urine despite large differences in their relative concentrations. Furthermore within the critical ranges indicated the system was designed to be maximally responsive to changes in the E13G/PD3G molar ratio of between 0.02 to 0.1, provided the assay was carried out at a pre-determined dilution of urine (or range of dilutions).

This was achieved by examining the dose-response characteristic of the dual analyte assay. Standard solutions of both E13G and PD3G were prepared in primary buffer to correspond to the physiological ranges and were tested as per assay protocol with the exception of PD3G standard solutions which were tested in the absence of anti-E13G in the primary reaction. A number of variables were investigated to determine their effect on:

(a) The change in signal intensity (absorbance) between the zero steroid standard and the highest steroid concentration.

(b) The signal to noise ratio of the response.

(c) The relative slope of each dose response curve (plotted as absorbance versus log dose).

(d) The position of the E13G dose-response curve compared to the position of the PD3G dose-response curve relative to the log dose axis. Some of the variables investigated were as follows:

(1) Nature of the MSA: effect of varying bridge length between E13G and PD3G moieties.

$MSA_4$, $MSA_6$, $MSA_8$ and $MSA_{10}$ were tested over a concentration range of 0.2 to 10 nM by the dual analyte assay protocol (excepting the absence of anti-E13G). $MSA_6$ resulted in the highest binding of AEP to SPAP (FIG. 2), $MSA_4$ resulted in 28 to 46% lower binding and both $MSA_8$ and $MSA_{10}$ gave 10% or less of the binding exhibited by $MSA_6$. Clearly bridge length between the two steroid groups of the MSA was crucial. Bridge lengths shorter than six methylene carbons restrict the simultaneous binding of both SPAP and AEP to the MSA. Whereas bridge lengths greater than six methylene carbons become long enough for the bridge to fold back on itself, thus again sterically hindering the simultaneous binding of both SPAP and AEP. $MSA_6$, with a hexamethylene bridge, was thus selected as the preferred reagent for the dual analyte assay.

(2) $MSA_6$ Concentration

PD3G dose-response characteristics were examined over a range of $MSA_6$ concentrations, from 0.2 to 20 nM. All curves showed an inverse relationship between PD3G concentration and signal intensity. They all were characterised by a plateau region between 0 and 10 nM PD3G with little fall in AEP binding, followed by a linear fall (on the log-linear plots) between 10 and 1000 nM PD3G. MSA concentrations of 2 nM and below produced the steepest slopes i.e. the more responsive systems. However for MSA concentrations below 1 nM severe reductions in overall signal intensity were observed.

E13G dose-responsive characteristics were examined over a similar range of MSA concentrations. In this case a direct relationship was observed between E13G concentration and absorbance readings. Again the position of each curve was little affected by MSA concentration; the steepest and hence most responsive range of the curves covered 1 to 10 nM E13G. However at MSA concentrations of less than 1 nM the slope became less pronounced. For MSA concentrations greater than 1.2 nM the signal to noise components of the curves became worse. $MSA_6$ at 1.2 nM was therefore the preferred concentration of this reagent.

(3) Anti-E13G Concentration

For each E13G anti-serum used in the dual analyte assay an optimal dilution factor has to be determined experimentally before it was included as a reagent in the primary reaction. Anti-E13G was diluted over the range 5000-fold to 25,000-fold as related to its final dilution in the primary reaction. E13G dose-response was examined at a number of anti-E13G dilutions.

As the dilution factor of anti-E13G increased so the position of the E13G dose-response curve shifted to the left, i.e. it became more responsive to lower E13G concentrations. However this effect was counterbalanced by a decreasing difference in signal intensity across the range of E13G concentrations. Also the signal to noise characteristics became worse. An optimum E13G dose-response curve was obtained at 7500-fold diluted anti-E13G.

A range of E13G and PD3G standard solutions were tested according to the dual analyte assay protocol. The resulting dose-response curves are shown in FIG. 3. The steepest regions of each curve are separated enough to allow a good response to the physiologically important E13G/PD3G ratio range.

For instance, say, menstrual cycle urines were tested at 25-fold diluted urine, then early follicular phase E13G concentrations (20 nM) would fall at the lower end of the E13G curve at around 0.8 nM. However, rising late follicular phase E13G concentrations should readily be detected since they would fall on the steepest region of the E13G curve at around 4 nM. Conversely during the follicular phase PD3G concentrations at 1000 nM or less would produce no more than say 40% depression of signal (at around 40 nM). But by the mid-luteal phase of the cycle PD3G concentrations should depress the signal by say 70% and approach absorbance values observed in the early follicular phase.

In order to simulate dose-response characteristics of the dual analyte assay which reflect changes in the E13G/PD3G ratio across a menstrual cycle, a matrix of E13G and PD3G standard solutions were made up and tested by the standard protocol.

FIG. 4 depicts an E13G dose-response curve in the presence of a low PD3G concentration (40 nM). This situation could well exist in the follicular phase in say 25-fold diluted urine samples. Notably E12G/PD3G values of 0.02 or less, representing the physiological baseline, all fall at the bottom, rather flat, region of the curve. Value of 0.03 or greater which are observed during a typical pre-ovulatory oestrogen surge, all fall on the steepest region of the E13G dose-response curve and are therefore readily detected.

The second curve depicts increasing PD3G concentrations in the presence of high E13G concentrations. This situation could well exist in the luteal phase of a menstrual cycle. A 10-fold increase in PD3G concentration brings the signal down to almost early follicular phase values.

An advantage of determining a ratio is that the result is independent of a volume dimension, which implies the result should be independent of sample dilution. In the case of the dual analyte assay, the result is not totally independent of sample dilution since the responsive range of the dose-response curves is not much more than one order of magnitude. However, over certain limits the dual analyte assay is reasonably tolerant of sample dilution. Standard solutions of E13G and PD3G were made up to give four ratios between 0.02 and 0.2 representing concentrations typical of menstrual cycle urine. These were tested by the dual analyte assay at 5-fold, 10-fold, 25-fold and 33-fold dilution factors. Results are given as follows:

| E13G/PD3G Ratio | Relative Signal (Mean ± s.d.) Dilution range × 5 to × 33.3 |
|---|---|
| 0.02 | 22.2 ± 2.2 |
| 0.04 | 28.5 ± 1.1 |
| 0.12 | 36.2 ± 3.4 |
| 0.2 | 43.9 ± 6.0 |

The tolerance of the assay to sample dilution is sufficiently broad to cope with most fluctuations in urine volume production.

The dual analyte assay has been used to monitor the relative changes in the E13G/PD3G ratio across a number of menstrual cycles where urine samples have been tested on a daily basis. The results obtained for a typical cycle are shown in FIG. 5. The graph is plotted as absorbance relative to control well absorbance against day of cycle. This subject was also monitored by ultrasonography to determine the time of ovulation. Since the ultrasonography was performed once per day there was a 24 hour uncertainty in this event which is indicated by the vertical broken lines on the graph.

The absorbance profile across the cycle shows a well defined surge over the 4 days immediately prior to the time of ovulation, rising to a peak value 1 day before ovulation. This is followed by a rapid fall after ovulation and a marked depression of absorbance during the luteal phase. The early follicular phase shows a minor peak, this is a common event and probably represents follicular acitivity. However, this major peak dominates the cycle and provides a clear marker both for determining the fertile period and for predicting imminent ovulation.

FIG. 6 summarizes results obtained when the dual analyte assay was used to measure daily urine samples from a total of 17 menstrual cycles.

In the Figure;

|   |   |
|---|---|
|   | indicates the start of the subject's menstrual cycle, |
|   | indicates the end of the subject's menstrual cycle, |
| O | indicates the day upon which the subject's basal body temperature was observed to rise, |
| U | indicates cycles in which the time of ovulation was estimated by ultrasonography. Follicle rupture occurred during the 24 hr period demarcated by the two vertical parallel broken lines. |
| B | indicates cycles in which the time of ovulation was estimated by the day of basal body temperature rise, this occurring on the day indicated by the dotted vertical line, |

An arbitary threshold value of relative absorbance was selected (35% relative to control wells) in order to highlight those days of the cycles when raised absorbance values were observed.

The threshold was exceeded in all 17 subjects either on the day of ovulation or several days before (up to 8 days). The fall below the threshold was observed in most subjects by two days after ovulation. During the luteal phase or early follicular phase the threshold was not exceeded.

These results indicate that a threshold value of the signal produced by the dual analyte assay could be chosen which is universal to all menstrual cycle urines. The dual analyte assay thus forms the basis of a yes/no type test to indicate whether or not a woman is in a fertile phase of her menstrual cycle.

We claim:

1. An assay involving the following components;
   a sample solution containing a first and a second antigenic solute;
   a first antibody capable of reversibly binding to a determinant of the first antigenic solute, the first antibody being in solution;
   a second antibody capable of reversibly binding to a determinant of the second antigenic solute, the second antibody being irreversibly bound to a solid phase support;
   a ligand molecule comprising a first antigen to which the first antibody is capable of reversibly binding and a second antigen to which the second antibody is capable of reversibly binding, the first and second antigens being irreversibly bound together through a bridging support molecule, the ligand molecule being in solution; and
   a labelled antibody capable of reversibly binding to the antigen,
   the assay comprising the steps of;
   forming a mixture of the sample solution, the first antibody, the second antibody and the ligand molecule, provided that the first antibody, the second antibody and the ligand molecule are not all mixed with each other prior to admixture of the sample solution;

incubating the said mixture, thereby allowing competition between the ligand molecule and the first antigenic solute for association with the first antibody and allowing competition between the ligand molecule and the second antigenic solute for association with the second antibody;

placing the solid phase support in contact with the labelled antibody, thereby allowing association between the labelled antibody and any unbound first antigen; and determining the amount of labelled antibody bound to the solid phase support through the ligand molecule and the second antibody.

2. An assay according to claim 1 wherein the ligand molecule comprises one first antigen and one second antigen, the two antigens being irreversibly bound together through a bridging support molecule.

3. An assay according to claim 1 wherein the mixture is formed by mixing the separate components in one step.

4. An assay according to claim 1 wherein the mixture is formed by;

forming a mixture of the sample solution and the ligand molecule, and mixing the said mixture with a mixture formed between the first antibody and the second antibody.

5. A method for determining the fertile period of the menstrual cycle comprising monitoring the relative concentration of oestrone-3-glucuronide and pregnanediol-3-glucuronide in urine with an assay as defined in claim 1.

6. A method according to claim 5 wherein the ligand molecule used in the assay comprises, at least one molecule of oestrone-3-glucuronide and at least one molecule or pregnane-3-glucuronide irreversibly bound through a bridge support molecule.

7. A method according to claim 5 wherein the ligand molecule is of the formula

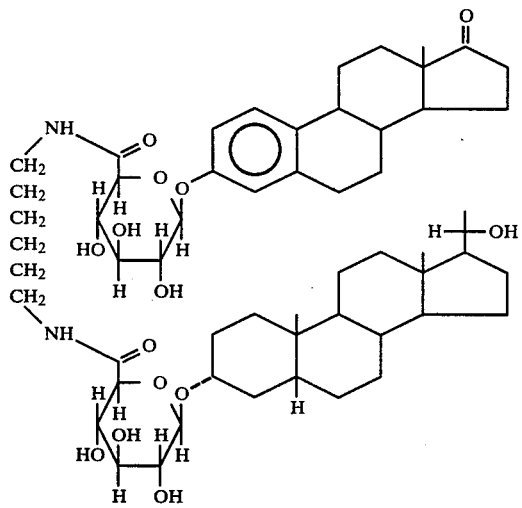

8. A reagent kit for performing an assay according to claim 1 or a method according to claim 5 comprising containers each containing, separately, or in combination, the first antibody, the second antibody or the ligand molecule provided that the first antibody, the second antibody and the ligand molecule are not present as a mixture together in a container, and a further container containing the labelled antibody.

9. A reagent kit for performing an assay according to claim 1 or a method according to claim 5 comprising:
a first container containing the first antibody,
a second container containing the second antibody,
a third container containing the ligand molecule, and
a fourth container containing the labelled antibody.

10. A reagent kit for performing an assay according to claim 1 or a method according to claim 5 comprising:
a first container containing the first antibody and the second antibody,
a second container containing the ligand molecule, and
a third container containing the labelled antibody.

11. A ligand molecule comprising two different antigenic radicals irreversibly bound to a bridging support molecule, the bridging support molecule being a divalent radical derived from an organic compound having two reactive functional groups.

12. A ligand molecule according to claim 11 wherein the divalent radical is derived from a compound of the general formula R(CH$_2$)$_n$R wherein R is —NH$_2$, —halogen, or —O—CO-alkyl and n is 2 to 10.

13. A ligand molecule according to claim 11 wherein R is —NH$_2$.

14. A ligand molecule according to claim 11 wherein n is 6.

* * * * *